United States Patent [19]

Beers et al.

[11] 4,438,039
[45] Mar. 20, 1984

[54] TITANIUM CHELATE CATALYST FOR SILICONE COMPOSITIONS

[75] Inventors: Melvin D. Beers, Schenectady; Richard P. Surprenant, Troy, both of N.Y.

[73] Assignee: General Electric Company, Waterford, N.Y.

[21] Appl. No.: 165,327

[22] Filed: Jul. 2, 1980

[51] Int. Cl.³ .............................................. C07F 7/28
[52] U.S. Cl. ............................ 260/429.5; 260/429 J; 528/17; 528/18; 528/19; 528/34; 502/171
[58] Field of Search ................... 260/429.5, 429 J; 252/431 R, 431 C

[56] References Cited

U.S. PATENT DOCUMENTS

| | | | |
|---|---|---|---|
| 3,006,941 | 10/1961 | Mudrak et al. | 260/429.5 X |
| 3,294,739 | 12/1966 | Wayenberg | 528/17 |
| 3,334,067 | 8/1967 | Wayenberg | 528/17 |
| 3,499,859 | 3/1970 | Matherly | 524/701 |
| 3,542,901 | 11/1979 | Cooper et al. | 528/33 |
| 3,689,454 | 9/1972 | Smith et al. | 528/17 |
| 3,694,475 | 9/1972 | Brook et al. | 260/429.5 |
| 3,779,986 | 12/1973 | Smith et al. | 260/37 SB X |
| 3,856,839 | 12/1974 | Smith et al. | 260/429.5 |
| 3,892,791 | 7/1975 | Brook et al. | 260/429.5 |
| 4,100,129 | 7/1978 | Beers | 260/37 SB |
| 4,113,757 | 9/1978 | Kay | 260/429.5 |

*Primary Examiner*—Helen M. S. Sneed

[57] ABSTRACT

A titanium chelate catalyst for a room temperature vulcanizable silicone rubber compositions which does not form nodules upon storage where the catalyst has the formula,

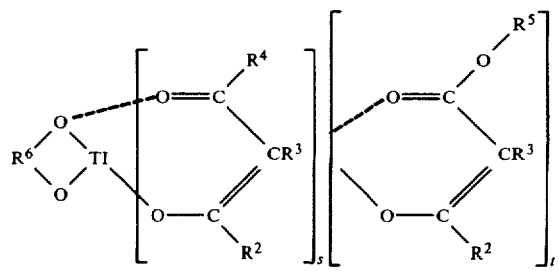

where s varies from 0.7 to 1.3 and t varies from 0.7 to 1.3. Preferably s varies from 0.8 to 1.2 and t varies from 0.8 to 1.2.

25 Claims, No Drawings

TITANIUM CHELATE CATALYST FOR SILICONE COMPOSITIONS

BACKGROUND OF THE INVENTION

The present invention relates to room temperature vulcanizable silicone rubber compositions and more particularly the present invention relates to a titanium chelate catalyst for room temperature vulcanizable silicone rubber compositions.

One component room temperature vulcanizable silicone rubber compositions are well known. Such compositions generally comprise a silanol end-stopped diogranopolysiloxane polymer, an acyloxy cross-linking agent and a tin salt as the catalyst. The composition was stored in one package in substantially anhydrous state. When it is desired to cure the composition the package is broken and upon exposure to atmopsheric moisture, the composition cross-links to form a silicone elastomer. Most recently, in the case of the acyloxy functional one component room temperature vulcanizable silicone rubber composition there has been developed an alkoxy functional one component room temperature vulcanizable silicone rubber composition (hereinafter room temperature vulcanizable will be referred to as RTV). Accordingly, Nitzche et al disclosed in U.S. Pat. No. 3,065,194 a family of silicone rubber compositions comprising a diorganopolysiloxane polymer having silanol end-stopped groups, an alkoxy functional cross-linking agent and a metal salt chelate organo metallic compound as a base that would serve as the cross-linking catalyst. There have been additional disclosures of one component alkoxy functional RTV compositions such as Brown et al U.S. Pat. No. 3,161,614 which shows a prereacted silanol end-stopped diorganopolysiloxane polymer in combination with the cross-linking catalyst. Cooper et al U.S. Pat. No. 3,383,355 disclosed the preparation of an alkoxy terminated linear siloxane polymer having a solid catalyst, e.g. fuller's earth. U.S. Pat. No. 3,499,859 discloses a hydrocarboxy end-blocked diorganopolysiloxane polymer and a metal containing curing catalyst along with boron nitride. Cooper et al U.S. Pat. No. 3,542,901 discloses a mixture of a linear siloxane having di or trifunctional end-blocking units and a linear siloxane having chemically non-functional inert end-blocking units on one end and di or trifunctional end-blocking units at the other end and including catalyst and the cross-linking agent. Brown et al U.S. Pat. No. 3,122,522 discloses organopolysiloxane intermediates containing condensation and condensable cellosolvoxyl with a catalyst. Brown et al U.S. Pat. No. 3,170,894 discloses organopolysiloxane intermediates containing condensable polyhydrocarboxy radicals with a catalyst and Weyenberg, U.S. Pat. No. 3,175,993 discloses organopolysiloxane intermediates end-blocked with alkoxylated silcarbane groups with a catalyst. However, there was a disadvantage with the catalyst for the above alkoxy systems in that the titanium salts that were disclosed tended to gell the composition and also resulted in an undesirable viscosity build-up during mixing and during storage of the composition for long periods of time. Accordingly, Smith and Hamilton U.S. Pat. No. 3,689,454 and U.S. Pat. No. 3,779,986, Weyenberg U.S. Pat. Nos. 3,294,739 and 3,334,067 and Clark et al U.S. Pat. No. 3,719,635 disclose alkoxy curing compositions in which they utilize a titanium ester chelate catalyst instead of the metal salts of the earlier patents wherein such titanium chelate catalyst controls the gellation and undesirable viscosity build-up during mixing and storage of the compositions for long periods of time such as one to two years. It should be noted that the earlier patents, Weyenberg U.S. Pat. Nos. 3,294,739 and 3,334,067 disclose titanium chelate catalysts which were advantageously utilized with one component alkoxy RTV compositions to produce suitable curing compositions. It should be noted that without the titanium chelate catalyst or some type of titanium salt the alkoxy one component RTV compositions cure too slowly. Subsequent to the discovery of Weyenberg and as disclosed in Smith and Hamilton U.S. Pat. Nos. 3,689,454 and 3,779,986 there was developed a titanium chelate catalyst which was substantially different from the earlier Weyenberg catalyst. Not only did the titanium chelate catalyst of those patents have the same advantageous properties as the Weyenberg catalyst but in addition it imparted to the resulting cured silicone elastomer more advantageous physical properties in terms of tensile strength, elongation, tear, and Durometer.

Then there was a further development in the art as disclosed in Beers U.S. Pat. No. 4,100,129. This patent utilizes substantially the same components as in the former Smith and Hamilton patent but by varying the catalyst to cross-linking agent weight ratio in the composition, there was obtained a composition with exceptionally low modulus and with exceptionally superior adhesion to various substrates. It should be noted that such compositions have been commercialized and have proven to be very successful in the commercial construction sealant market.

However, it was noted after these materials had been marketed for some time, that their shelf lives were largely determined by an appearance problem manifesting itself in the formation of various sizes of crystals ranging from fine sand-like to pellet-like particles. These pellets did not affect the performance of the sealant especially when the sealant was to be used for construction purposes although it did give an unsightly appearance, in the surface texture of the sealant. However, when the sealant was pumped through sealant application lines which were terminated with small outlets these nodules would tend to plug up the orifice thus causing malfunction of mixing and application equipment. It was determined through experimentation and analysis of these nodules that the formation of these nodules usually take six to eight months although a significant number of compositions would not contain them. It was determined that the nodules could be prevented from forming by freezer storage of the compositions prior to use. While such storage was suitable for the utilization of industrial sealants, that is sealants that were to be utilized in factories, it was not found to be a suitable method of nodule prevention for sealants that were to be utilized in construction because the construction sealant distribution network does not have freezer storage available. Accordingly, it was decided to find a way to prevent these nodules from forming.

It must be understood that the explanation given below of nodule formation is merely a theory which seems to be substantiated by the facts and at any rate the nodule problem has been solved as will be pointed out below. Accordingly, proceeding along with our explanation of nodule formation there was utilized 1,3 dioxypropane titanium bis ethylacetoacetate, methyltrimethoxy silane cross-linking systems. Both of these liquid materials reacted to form a titanium chelate with a lower degree of solubility in the system. This occurred due to the following reaction:

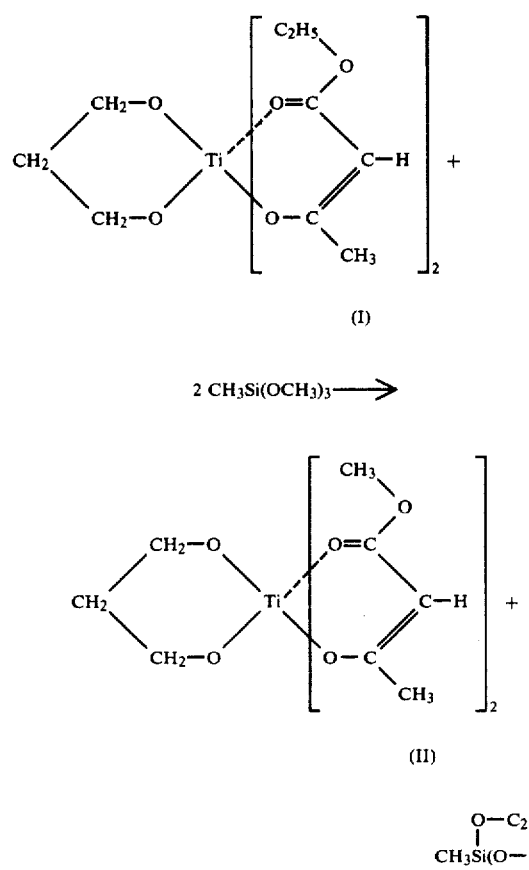

The resulting methylester titanium chelate of formula II is less soluble than that of formula I which is the catalyst that is inserted in the system. The (II) catalyst version complexes with the filler in the sealant which leads to the the formation of nodules. It was decided that there were four possible approaches to preventing such nodule formation and specifically to prevent the formation of the titanium chelate catalyst of formula II above. These approaches were to utilize a solvent, the possible addition of some amounts of ethanol or ethyl silicate to discourage the above reaction, changing to a titanium chelate which could not undergo the reaction as shown above and finally the preparation of a new mixed chelate.

The first approach which was tried was the solvent approach with toluene or acetonitrile. This approach was successful but was discarded for toxicity and sealant shrinkage problems. The second approach retarded the cure and shortened the shelf-life of the sealant and therefore was discarded. The third approach involved the preparation of 1,3-dioxypropane titanium bis-acetylacetonate of the formula,

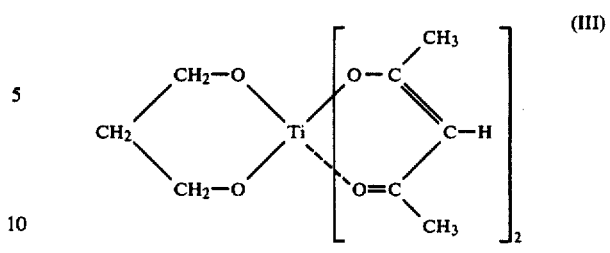

In the laboratory the third approach was promising except that even this material upon standing for six to nineteen months would complex with small amounts of sediment that formed in the production storage tanks as the result of some natural precipitation processes that are bound to occur. It should be noted that the titanium chelate catalyst in (III) above had to be heated to approximately 40±5° C. to keep the titanium chelate catalyst in solution. Accordingly because of the lack of solubility of the titanium chelate catalyst of Formula (III) even this catalyst would come out of solution and react with minor amounts of sediment to form nodules. Accordingly, it was discovered after much experimentation that the best approach and the best titanium chelate catalyst which would have all the foregoing properties of the Smith and Hamilton and Beers patents mentioned previously but which would have prolonged storage of up to four years or more without the formation of nodules was the utilization of a mixed titanium chelate system.

Accordingly, it is one object of the present invention to provide for a titanium chelate catalyst that does not form nodules even upon standing for periods of three or four years or more.

It is another object of the present invention to provide for a titanium chelate catalyst that is inexpensive to make and does not present gellation problems and still does not form nodules in room temperature vulcanizable silicone rubber compositions.

It is still an additional object of the present invention to provide for alkoxy functional one component RTV compositions having a titanium chelate catalyst which composition does not form nodules for periods of three to four years upon storage prior to cure.

It is yet an additional boject of the present invention to provide a process for producing a titanium chelate catalyst which is relatively inexpensive and efficient which titanium chelate will not form nodules in RTV composition for prolonged periods of time.

It is an additional object of the present invention to provide a process for forming a one component RTV composition which has a novel titanium chelate catalyst in it which will prevent the formation of nodules in the composition for periods of three to four years or more upon standing prior to cure.

These and other objects of the present invention are accomplished by means of the disclosure set herein below.

SUMMARY OF THE INVENTION

There is provided by the present invention in accordance with the above objects a titanium chelate catalyst for room temperature vulcanizable silicone rubber compositions which does not form nodules upon standing prior to cure comprising a first reaction product formed from a titanium compound of the formula, $$\text{Ti(OR)}_4 \qquad (1)$$

which is reacted with a first ketone compound of the formula, $$R^2-\overset{O}{\overset{\|}{C}}-CR^3\overset{H}{\overset{|}{-}}\overset{O}{\overset{\|}{C}}-R^4 \qquad (2)$$

and a second ketone compound of the formula $$R^2-\overset{O}{\overset{\|}{C}}-CR^3\overset{H}{\overset{|}{-}}\overset{O}{\overset{\|}{C}}-O-R^5 \qquad (3)$$

where R, $R^2$, are substituted or unsubstituted monovalent hydrocarbon radicals, $R^3$ is selected from the group consisting of hydrogen, hydrocarbyl, halohydrocarbyl and, acyl, all having not more than 8 carbon atoms and taken together with $R^2$ forms together with the carbon atoms to which they are attached cyclohydrocarbon substituents of not more than about 12 carbon atoms and chloro, nitro, acyl, cyano, and carboxy ester substituted cyclic hydrocarbon substituents, $R^4$ is a radical selected from the class consisting of radicals having not more than about eight carbon atoms selected from the group consisting of hydrocarbyl, halohydrocarbyl, cyanoalkyl, and amino and $R^5$ is selected from the class consisting of monovalent hydrocarbon radicals, amino, ether and polyether moieties of the formula, $$-(C_qH_{2q}O)_vR^{30} \qquad (4)$$

where q varies from 2 to 4 and v varies from 1 to 20 and $R^{30}$ is a monovalent hydrocarbon radical which first reaction product is then reacted with a diol of the formula, $$HO-R^6-OH \qquad (5)$$

to produce the second and final reaction product where $R^6$ is a divalent hydrocarbon radical of 2 to 20 carbon atoms.

The term monovalent hydrocarbon radical includes halohydrocarbyl radicals and all types of various hydrocarbon radicals that may be appended as shown in the specification and claims. The titanium chelate catalyst is claimed as a reaction product of certain reactants as most of the catalyst is of the composition shown in the formula disclosed below; however, a small portion of the catalyst will not be of such formula.

It should also be noted that the titanium chelate catalyst may also be a physical blend of the two types of catalyst. Accordingly, there may be present in the titanium chelate catalyst for room temperature vulcanizable silicone rubber composition which does not form nodules upon standing prior to cure comprising the physical blend of the titanium chelate catalyst of the formula,

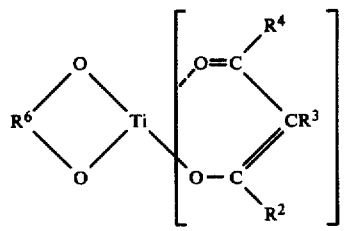

(6)

and a second titanium chelate catalyst of the formula,

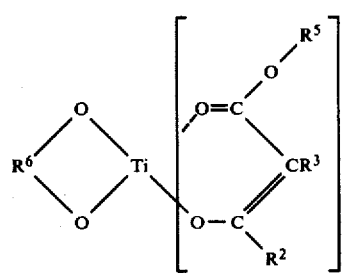

(7)

In the above physical blend the first catalyst is present at a concentration of 35 to 65 mole percent based on the total catalyst system. Preferably and more generally the first catalyst may vary at a concentration of 40 to 60 mole percent based on the total titanium chelate system. Again this physical blend will have some impurities in it as a result of the way the individual chelate catalyst are made. The invention of the instant case covers room temperature vulcanizable silicone rubber compositions and, more particularly, one component RTV compositions which are alkoxy functional and which contain the physical blend of the titanium chelate catalyst in it. Such a physical blend will function just as effectively as the reacted catalyst system to produce a system that does not form nodules for a prolonged period upon standing prior to cure.

DESCRIPTION OF THE PREFERRED EMBODIMENT

In the basic composition there is present a silanol end-stopped diorganopolysiloxane polymer of a viscosity varying from 100 to 1,000,000 centipoise at 25° C. where the organo groups are monovalent hydrocarbon radicals. Preferably the viscosity varies from 100 to 500,000 centipoise and more preferably the viscosity varies from 100 to 100,000 centipoise at 25°. The organo group can be any monovalent hydrocarbon radical normally associated with substituent groups for polysiloxanes, for example, alkyl radicals of 1 to 8 carbon atoms such as methyl, ethyl, propyl, etc.; cyclo alkyl radicals such as cyclohexyl, cycloheptyl, cyclooctyl and so forth; alkenyl such as vinyl, allyl and so forth; mononuclear aryl radicals such as phenyl, methylphenyl, ethylphenyl and so forth; and fluoroalkyl radicals such as 3,3,3-trifluoropropyl. The polymer may have up to 10 percent by weight of trifunctionality. To obtain an RTV composition with the most desirable properties it is preferred that the silanol end-stopped diorganopolysiloxane polymer have the formula,

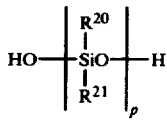 (8)

where $R^{20}$ and $R^{21}$ are monovalent hydrocarbon radicals and where p varies sch that the viscosity of the polymer varies from 100 to 1,000,000 centipoise at 25° C. and more preferably varies from 100 to 500,000 at 25° centipoise. Most preferably p varies such that the polymer has a viscosity varying from 100 to 100,000 centipoise at 25° C. The $R^{20}$ and $R^{21}$ groups may be the same or different and are generally selected from the same groups as the monovalent hydrocarbon radicals defined previously for the organo groups of the diorganopolysiloxane polymer. Preferably at least 50 percent of the total number of $R^{20}$ and $R^{21}$ radicals are alkyl radicals of 1 to 8 carbon atoms and any remaining groups are aryl radicals.

Most preferably the alkyl radicals are methyl radicals and the remaining aryl radicals are phenyl radicals. Most preferably, the $R^{20}$ and $R^{21}$ radicals are selected from alkyl radicals of 1 to 8 carbon atoms such as methyl or from a mixture of alkyl radicals of 1 to 8 carbon atoms and fluoroalkyl radicals such as 3,3,3-trifluoropropyl. Per 100 parts of a silanol end-stopped diorganopolysiloxane polymer, there is preferably present from 0.01 to 25 parts by weight of a cross-linking agent of the formula, $$R_m^{40}Si(O\,R^{41})_{4-m} \qquad (9)$$

where $R^{40}$ and $R^{41}$ are monovalent hydrocarbon radicals that can be any of the radicals defined previously for $R^{20}$ and $R^{21}$. Preferably $R^{40}$ is an alkyl radical of 1 to 8 carbon atoms and $R^{41}$ is an alkyl radical of 1 to 8 carbon atoms, m has a value of 0 to 3 and preferably m has a value based on the total amount of silanol in the composition of 0 to 1.99. Most preferably m is equal to 1 and $R^{40}$ and $R^{41}$ are methyl. Illustrative of such cross-linking agent which can be utilized in the RTV composition of the invention are the following:

$CH_3Si(OCH_3)_3$
$CH_3Si(OCH_2CH_3)_3$
$(CH_3)_2Si(OCH_3)_2$

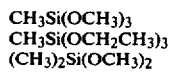

$Si(OCH_3)_4$

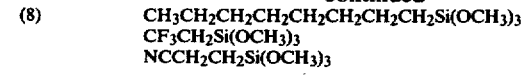

These silanes are well known in the art and are described for example in Berridge U.S. Pat. No. 2,843,555.

The third necessary ingredient in the composition is present in the concentration of 0.1 to 10 parts by weight of the base composition is the titanium chelate catalyst reaction product. In the chelate catalyst the metal need not be titanium.

It can be selected from lead, tin, zirconium, antimony, iron, cadmium, barium, bismuth, manganese, zinc, chromium, cobalt, nickel, aluminium, and gallium or germanium. However, the most preferable metal is titanium. Accordingly, there may be present from 0.1 to 10 parts by weight of the titanium chelate catalyst. The titanium chelate catalyst has been defined in the Summary of the Invention in terms of a reaction product of certain reactants. Most of the reaction product is a compound of the formula,

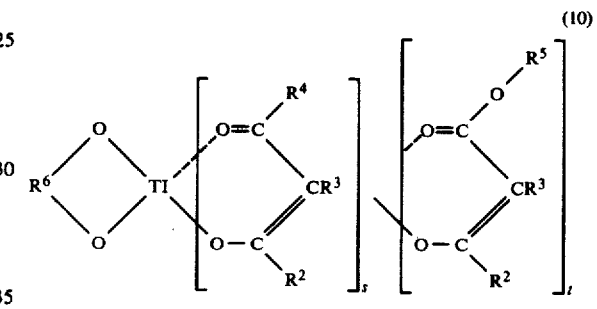 (10)

where s varies from 0.7 to 1.3. Most preferably s varies from 0.8 to 1.2 and t varies from 1.2 to 0.8. The most preferable compound or reaction product is one in which in the formula s is equal to 1 and t is equal to 1. However, as pointed out previously, what has been claimed as the reaction product of certain reactants is the titanium catalyst since such reaction product includes the individual chelates as will be explained below. In the formula of the preferred titanium chelate, preferably $R^6$ is propane and $R^3$ is hydrogen. Also, preferably $R^2$ and $R^4$ are methyl. The most preferred titanium chelate catalyst is one of the formula,

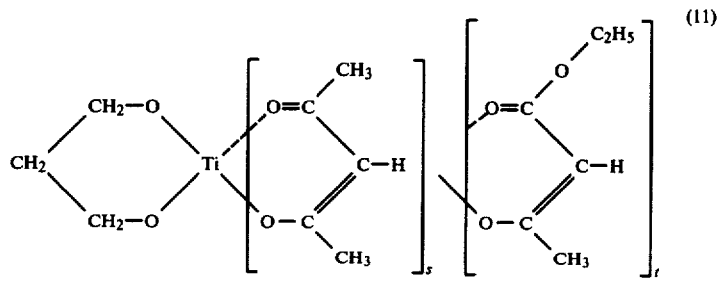 (11)

where as stated most preferably s is equal to 1 and t is equal to 1. It should be noted that $R^6$ is formula 10 is equivalent to the

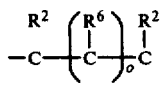

of the formula of the titanium chelate catalyst in U.S. Pat. No. 4,100,129 in column 7, line 25 through 30. It was not felt necessary to include this cyclic group in as much detail as was done in U.S. Pat. No. 4,100,129 and U.S. Pat. No. 3,689,454 since all the necessary details are in those patents and those patents are incorporated by reference in the present case. The group $R^6$ is a divalent hydrocarbon radical of 2 to 20 carbon atoms and may have hydrocarbon substituent groups of up to 8 carbon atoms including halohydrocarbon groups and carboxyl groups and in addition to hydrocarbon substituent groups in the middle portion of the $R^6$ group there may be other substituents groups such as halo, cyano, nitro, carboxy ester or acyl, and hydrocarbon substituent groups, substituted by halo, cyano, nitro, carboxy ester and acyl. The total number of carbon atoms in the $R^6$ group need not be more than 20 carbon atoms, but more preferably need not be more than 10 carbon atoms. The radical $R^3$ is preferably hydrogen or an organic radical of up to 8 carbon atoms selected from hydrocarbyl halohydrocarbyl and acyl and when taken with the $R^2$ groups forms together with a carbon atom to which they are attached a cyclic hydrocarbon substituent of about 12 carbon atoms or such a substituent group substituted with one or more chloro, nitro, ester, cyano or carboxy ester substituents. The radical $R^4$ is the same substituent group as $R^2$ however $R^5$ may be a radical of up to 20 carbon atoms selected from hydrocarbyl, halohydrocarbyl, cyanoalkyl, amino, ether, and polyether groups of the formula—$(C_qH_{2q}O)_vR^{30}$ where q varies from 2 to 4 and small v varies from 1 to 20 and a $R^{30}$ is the monovalent hydrocarbon radical. These compounds are normally produced by reacting betadicarbonyl compounds with the titanium compound to form a dialkoxy containing chelate. The dialkoxy containing chelate can then be reacted with the corresponding alkane diol to produce a wholly cyclic chelate compound. The preparation of such compounds is described in U.S. Pat. Nos. 3,689,454 and 3,779,986. Illustrative of the titanium chelate compounds with a single distinct chelate group on the right hand of the titanium atom is as follows:

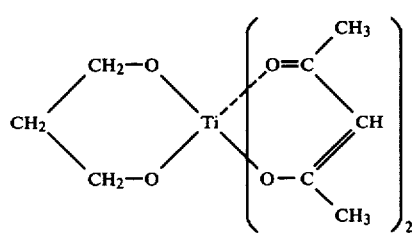

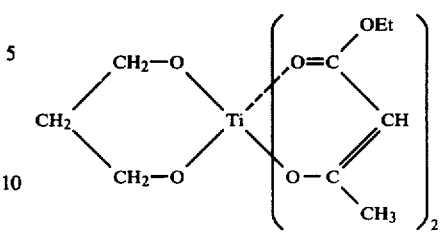

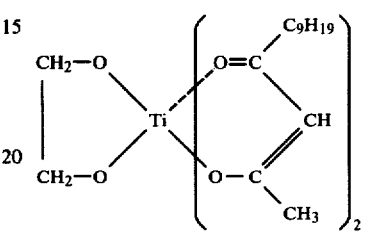

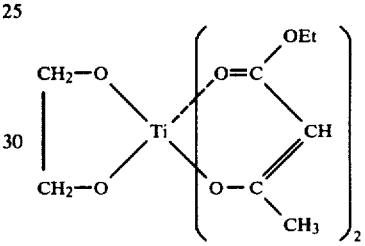

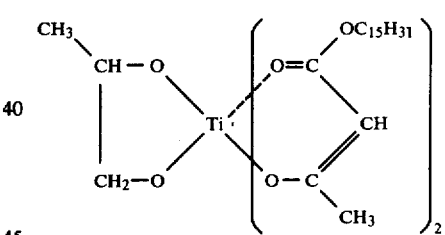

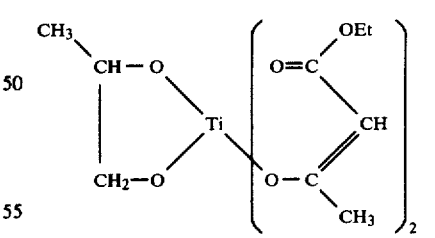

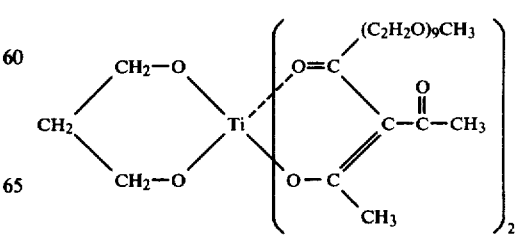

-continued

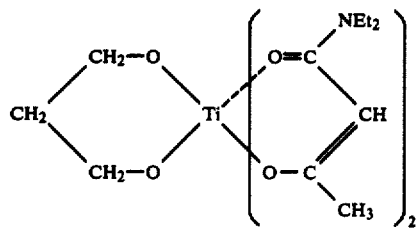

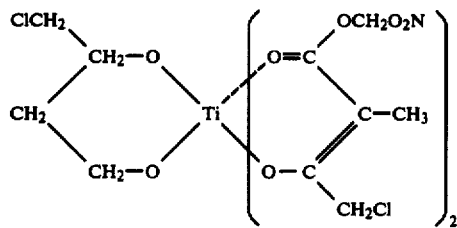

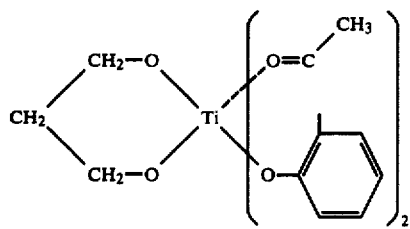

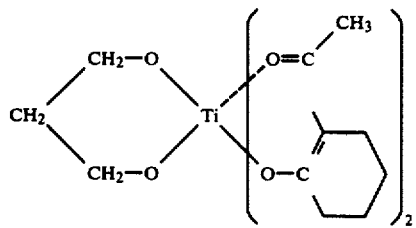

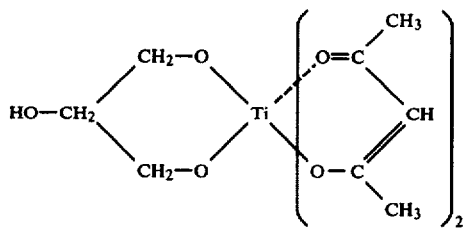

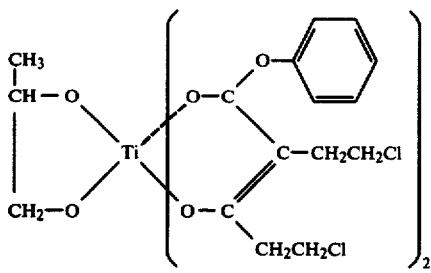

-continued

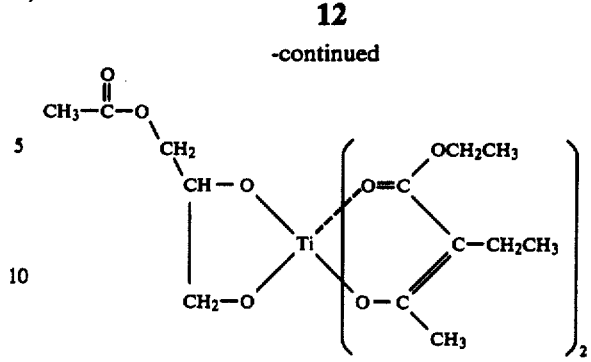

It should noted that the titanium chelate compounds of the above formula are the same as the compounds in the physical blends and are the same in the reaction products except the chelate version has two different types of chelates at the right hand portion of the titanium atom as has been described by the formulas shown above. These titanium chelate compounds, preferably the titanium compounds reaction products that are preferred, are produced by reacting one mole of a tetraalkoxy titanium compound of the formula, Ti(OR)$_4$ with a one mole of a betadicarbonyl compound or a first ketone compound of the formula

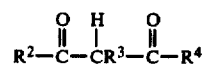

and with a second ketone compound of the formula

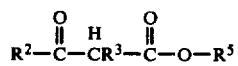

where the groups are previously defined. The resulting first or intermediate reaction product is then reacted with one mole of a diol of the formula,

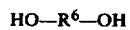

to produce the preferred titanium chelate reaction products of the instant case. It is preferred that when a dicarbonyl compound is a lower alkyl ester of an acetoacetic acid that the temperature be maintained below 70° C. in the reaction. The preferred dicarbonyl compounds are lower alkyl ester of acetic acid. The alkyl group can be straight chained or branched. The preferred group of acetoacetates include methylacetoacetate, ethylacetoacetate, propylacetoacetate, isobutylacetoacetate, pentylacetoacetate, hexylacetoacetate, heptylacetoacetate, and octylacetoacetatee. One of the preferred acetoacetate is ethyl acetoacetate. It is also preferred that R be an isopropyl radical as this alkoxy interchange produces isopropyl alcohol. The isopropyl alcohol can then be azeotropically distilled using toluene as the azeotroping agent in both the described reactions.

The use of a solvent is not necessary but is preferred Solvents other than toluene which can be employed include benzene, xylene, hexane or any other of the well known solvents useful for the azeotropic removal of formed alcohol from solution. It is noted that the preparation of the titanium chelate reaction product of the instant case is the same as the one set forth in U.S. Pat.

No. 3,779,986 and the worker skilled in the art is referred to that patent for specific details as to the preparation of such a titanium chelate catalyst in addition to what has been given above. An example of the reaction for preparing the preferred titanium chelate reaction product of the instant claims which is utilized as a catalyst and is preferably a catalyst in RTV compositions is as follows:

position in the quantities as set forth previously and also below. In the reaction product, it is not specified that both chelate compounds have to be reacted with the titanium compound at the same time. Accordingly, the reaction product covers the case where the titanium compound is individually reacted with each ketone compound and then combined and reacted with the diol.

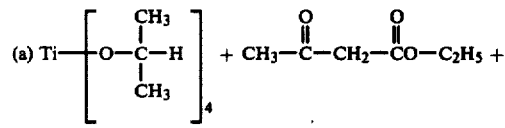

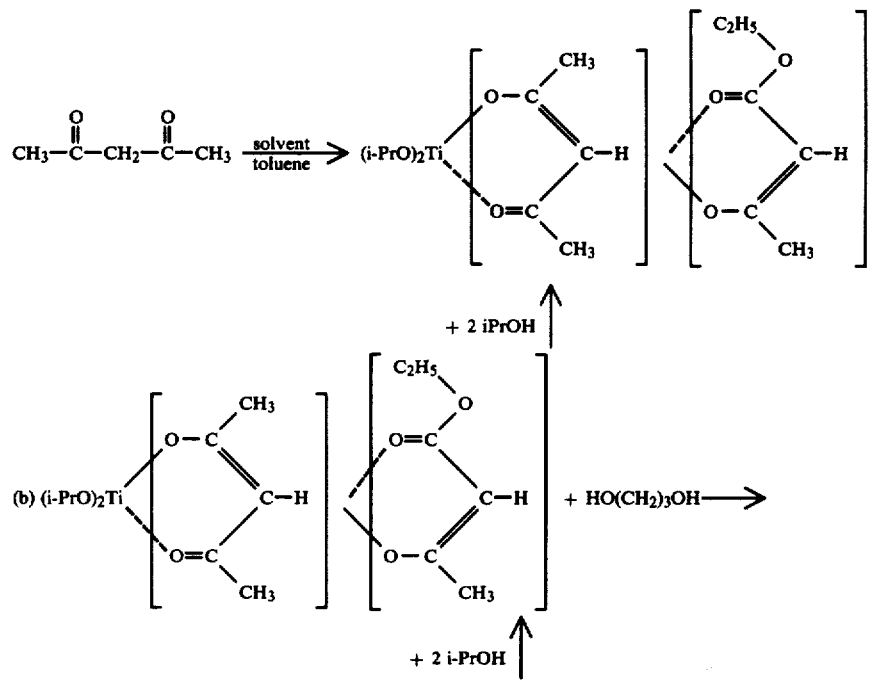

The above illustrates the reaction for preparing the preferred titanium chelate catalyst in the instant case. It should be noted that in Formula (10) for the titanium chelate catalyst above s and t are most preferably 1, but can vary within the range as set forth above. It can also be appreciated that the reaction product is a mixture of chelates most of which have the formula of the preferred titanium chelate catalyst as shown in the formula (10) and that in the reacted titanium chelate mixture there is some presence of the isoproxy compound and there is some amount of the individual chelates. It should be noted that the titanium chelate catalyst of the present case need not be a reaction product as set forth above but may be a physical blend of the individual chelates.

The $R^6$ group is the same as previously defined and can be the same in each chelate or different in the same way the $R^3$ and $R^2$ groups and each chelate can be the same or different from the other chelate. Thus in accordance with the present invention, the individual chelates can be individually prepared and then mixed together in the proper proportions and then added to the other components of the other composition to provide a suitable one component RTV composition.

Then the physical blend can be added as a catalyst in the proper quantities to the one component RTV com- Irrespective of whether the reaction product catalyst version is utilized or the physical blend of titanium chelate catalyst version is utilized, such catalyst will work suitably to prevent nodule formation in uncured RTV composition for periods as long as four years or more. To produce a one component RTV composition with high elongation and low tensile strength with adhesion to substrates, it is preferred to have in the composition per 100 parts of a silanol chainstopped polymer from 0.01 to 5 parts by weight of the cross-linking silane and from 0.1 to 10 parts by weight of a titanium chelate catalyst reaction product or physical blend as specified in U.S. Pat. No. 4,100,129. It should be noted that this is one version of a particular type of one component RTV composition to which the titanium chelate catalyst of the instant case can be applied. It should be noted that the titanium chelate catalyst of the instant case is not solely limited to the compositions of U.S. Pat. No. 4,100,129 but can be applied to any alkoxy functional one component RTV system. With respect to the composition of U.S. Pat. No. 4,100,129 to which the titanium chelate catalyst of the instant case can be suitably applied, this is one embodiment within the scope of the instant invention. In that case, it is preferred that the weight ratio of the titanium chelate catalyst of the instant case to the cross-linking agent be at least 0.5. More preferably the weight ratio of the titanium chelate catalyst of the instant case to the cross-linking can be 0.5:1 to 10:1. Still more preferably the weight ratio of the titanium chelate catalyst of the instant case to the cross-linking agent is from 0.5:1 to 5:1. For more details as to the weight ratio and to the preparation of such compositions, the reader is referred to U.S. Pat. No. 4,100,129 which is hereby incorporated by reference. Suffice to state that the titanium chelate of the instant case will work with advantage in the compositions of U.S. Pat. No. 4,100,129 as well as in the composition of U.S. Pat. Nos. 3,689,454 and 3,779,986; that is, one component alkoxy curing RTV compositions. Thus, there may be added metal salts of carboxylic acids as curing acelerators as pointed out in the foregoing patents. There may be added viscosity depressants as will be explained below. In addition there may be added silyl maleate, silyl fumerate, silyl succinate, adhesion promoters of Mitchell, DeZuba, and Smith patent Ser. No. 4,273,698 entitled "Self-Bonding Room Temperature Vulcanizable Silicone Rubber Compositions" and which disclosure is hereby incorporated by reference.

The RTV compositions of the present invention can also be modified by the incorporation of various extenders or fillers. Illustrative of the many fillers which can be empolyed with the compositions of the present invention are titanium dioxide, lithopone, zinc oxide, zirconium silicate silica aerogel, iron dioxide, diatomacious earth, calcium carbonate, fumed silica, silazane treated silica, precipitated silica, glass fibers, magnesium oxide, chromic oxide, zirconium oxide, aluminum oxide, crushed quartz, calcined clay, asbestos, carbon, graphite, cork, cotton, synthetic fibers, etc. Among the most useful fillers are calcium carbonate alone, or mixed with fumed silica. Organosilicone-or silazane-treated silica fillers, such as those described in Lucas, U.S. Pat. No. 2,938,009; Lichtenwalner, U.S. Pat. No. 3,004,859, and Smith U.S. Pat. No. 3,635,743 are also particularly suitable for use in the RTV compositions of the present invention. The fillers are generally employed in amounts from about 5 to about 200 parts, and preferably, from 10 to about 100 parts by weight per 100 parts of silanol chain-stopped polydiorganosiloxane component (a).

In addition to fillers, the present compositions can also optionally include an adhesion promoter, e.g., from 0.2 to 2 parts of such promoter per 100 parts of component (A). These will generally be nitrogen-containing compounds, silyl functional isocyanurates. A preferred class of promoters are those of the formula:

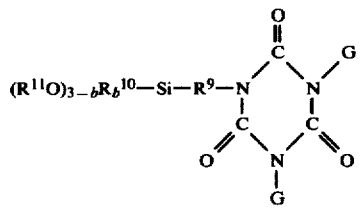

wherein G is the same as $R^{10}$, hereinafter defined, a

radical, styryl, vinyl, allyl, chloroallyl or cyclohexenyl; $R^9$ is a divalent radical selected from alkylenearylene, alkylene, cycloalkenyl and halosubstituted such divalent radicals; $R^{10}$ is a radical of up to 8 carbon atoms selected from hydrocarbyl or halohydrocarbyl and $R^{11}$ is a radical of the type defined for $R^{10}$ and also cyano lower alkyl; and b is 0 to 3. Such adhesion promoters are disclosed in the copending application of Berger, Ser. No. 301,637, filed Oct. 17, 1972, now abandoned, which is incorporated herein by reference. The most preferred promotors are 1,3,5-tris-trimethoxysilyl-propylisocyanate and bis-1,3-trimethoxysilyl-propylisocyanurate. In addition to fllers and adhesion promoters, the present compositions can also include a thixotrope or viscosity depressant in the form of from 0.3 to 20 parts by weight of a low molecular weight linear polydiorganosiloxane. A preferred class of such viscosity depressants has the formula:

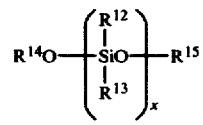

wherein $R^{12}$ and $R^{13}$ are each organic radicals of up to 8 carbon atoms selected from hydrocarbyl, halohydrocarbyl and lower cyano-alkyl, $R^{14}$ and $R^{15}$ are, independently, hydrogen or radicals as defined for $R^{12}$ and $R^{13}$, and x has a value of from 2 to 46. The most preferred such thixotropes are those of the above formula wherein, in the viscosity depressant, $R^{14}$ and $R^{15}$ are methyl, $R^{12}$ and $R^{13}$ are methyl or methyl and phenyl in a ratio of about 70:30, and x is an integer of from 3 to 50. Additional conventional ingredients can also be included, such as flame retardants, stabilizing agents, pigments, reinforcements, and the like. The compositions of this invention are stable in the absence of moisture. Consequently, they can be stored for prolonged periods of time without deleterious effect. During this period of storage, no significant change occurs in the physical properties of the room temperature vulcanizing compositions. This is especially advantageous commercially because it insures that once the composition is prepared with a given consistency and cure time, neither change significantly on storage. Storage stability is one of the characteristics which makes the present compositions valuable in one-package systems. The compositions prepared by mixing the metal ester catalyst and the silane with the silanol chain-stopped polydiorganosiloxanes under anhydrous conditions can be used without further modification in many sealing, caulking and coating applications merely by placing the compositions in the desired location and permitting them to cure upon exposure to the moisture present in the atmosphere. Upon such exposure, even after previous storage for many months, a "skin" will form on the present compositions within a relatively short time, e.g., from ½ to about 8 hours, and they will cure to a rubbery state within from a few hours to several days, at room temperature, e.g., 18° to 25° C. Where the compositions of the present invention contain ingredients other than the silanol-terminated polydiorganosiloxane, the silane cross-linker and the metal ester catalyst, these additional ingredients can be added in any desired manner. However, for ease in manufacturing, it is often most convenient to form a "base" blend of all of the components except the silane, the metal ester and, if present, the adhesion promoter, then to remove moisture from the base blend, e.g., by maintaining it under a vacuum and thereafter to add the silane, the metal ester and, optionally, the adhesion promoter, just prior to packaging in containers protected from moisture. The compositions of this invention are particularly suitable for caulking and sealing applications where excellent adhesion to a variety of substrates is important. For example, the compositions are useful in household and industrial caulking and sealing in buildings, factories, automobiles, and the like, and with substrates such as masonry, glass, plastic, metal, wood and the like. There is little or no tendency for the present compositions to corrode most metal substrates. They are also advantageous in having excellent rates of application, making them readily suitable for application from conventional caulkers under standard conditions. Other additives as they are developed may be added to this composition of the instant case to vary the properties as is desired or to produce a more advantageous composition.

The examples given below are given for the purpose of illustrating the present invention and they are not given below for purpose of setting means and boundaries to the scope of the claims of the specification. All parts in the examples are by weight.

EXAMPLE 1

Preparation of 1,3-propane-dioxy titanium (ethylacetoacetate), (acetylacetonate) 1 to 1 molar ratio

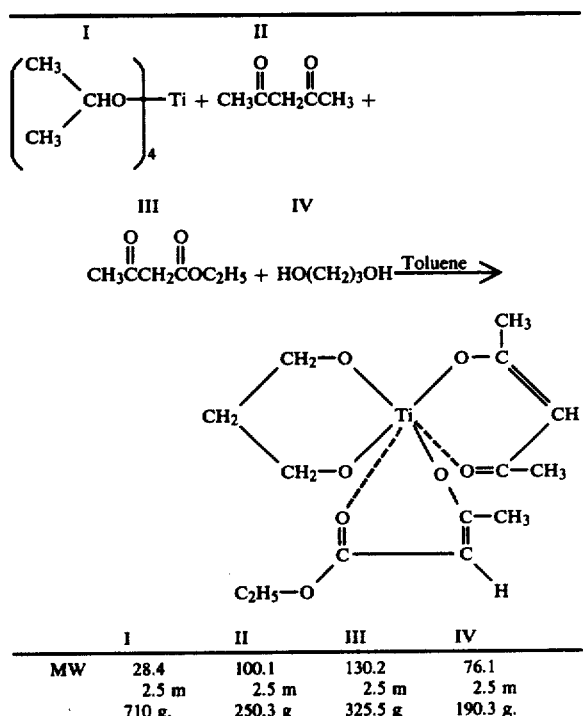

| | I | II | III | IV |
|---|---|---|---|---|
| MW | 28.4 | 100.1 | 130.2 | 76.1 |
| | 2.5 m | 2.5 m | 2.5 m | 2.5 m |
| | 710 g. | 250.3 g | 325.5 g | 190.3 g. |

In a 5 L-3 Neck flask equipped with a magnetic stirrer, heating mantle with thermal watch, 2 dropping funnels, pot thermometer, small packed column, Dean-Stark trap and a fractionating receiver with condenser was placed 860 parts. of $C_6H_5CH_3$ and 710 parts of tetraisopropyltitanate. The system was placed under 90 mm of pressure with a vacuum pump. The two chelating agents (ethylacetoacetate and acetylacetone) were mixed in one dropping funnel. Added fresh toluene to the other dropping funnel. Brought the pot to reflux and began adding the two mixed chelating agents slowly. A maximum temperature of 60° was maintained throughout the reaction. Removed the distillate at about a 5:1 reflux ratio during this addition. The total addition time was 3 hours. Brought the reflux ratio to 2:1 until the head take off temperature reached the boiling point of pure toluene. During this azeotrope process, fresh toluene was added in equal volume to the distillate removed.

Placed the 1-3 propanediol in the dropping funnel at this point. Added this material using the same procedure used to add the acetates. The addition time of the diol was 1.5 hrs. When the head take off temperature and the boiling point of pure toluene was reached, the system was switched to total take off. The reaction residue was then stripped to 60° C. @ 10 mm. Cooled residue to room temperature. The resulting desired product was a somewhat viscous yellowish liquid which was subsequently packaged in a clean, air tight storage bottle.

EXAMPLE 2

Preparation of 1,3-propane-dioxytitanium(ethyl cetoacetate,-acetylacetonate) 0.72 to 1.28 mole ratio.

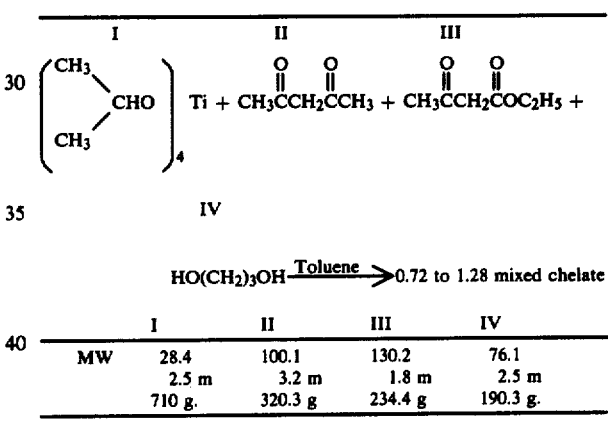

| | I | II | III | IV |
|---|---|---|---|---|
| MW | 28.4 | 100.1 | 130.2 | 76.1 |
| | 2.5 m | 3.2 m | 1.8 m | 2.5 m |
| | 710 g. | 320.3 g | 234.4 g | 190.3 g. |

This preparation was run identical to example 1 except that the ratio was adjusted. Catalyst appearance was also similar.

EXAMPLE 3

The following ingredients were mixed together under high shear conditions at room temperature for 5 hours; 100 parts of silanol-terminated polydimethylsiloxane of 100,000 centipoise at 25° C. viscosity; a polymer compound of 5 parts of 25 mole percent diphenylsiloxane units, 5 mole percent trimethylsiloxane units and 70 mole percent dimethylsiloxane units; 12 parts of octamethylcyclotetrasiloxane treated fumed silica; 120 parts of stearic acid treated calcium carbonate and 40 parts of trimethylsiloxy terminated dimethylsiloxane polymer of 100 centipoise at 25° C. The material was prepared under vacuum (ca 20 mm). This material is referred to as Composition A.

There was prepared a Composition B as follows: first to 1.8 parts of the chelate of Example 1 (1,3-propane-dioxytitanium(ethylacetoacetate, acetyacetonate) there were added 1.5 parts of methyltrimethoxysilane and 0.75 parts of 1,3,5-tri-trimethoxysilylpropylisocyanurate.

To 100 parts of Composition A was added 4 parts of composition B in an air and moisture free system. They were mixed until a smooth uniform composition was obtained. The material was packaged in air and moisture free containers.

A portion of this material was cured into ASTM molded slabs for 24 hours and air cured 75° C.±2° C. at 50±5% relative humidity for an additional 6 days. The slabs when tested had the following physical properties.

| Tensile strength, psi | 210 |
| Elongation, percent | 750 |
| Shore A, hardness | 25 |

The material was noted to have the following physicals:
  Tack Free Time, hrs.—7.0 hours
  Application Rate (90 p.s.i., through ⅛ orifice for 1 min.) grams/minute—220
  Boeing Flow Rate (Vertical sag for 3 minutes) inches—0.15
  Specific Gravity—1.40

The adhesion characteristics of this material were determined by peel adhesion testing. The surfaces were cleaned with appropriate solvents and coated with ⅛" of sealant. A wire mesh was imbedded in sealant and coated with ⅛" sealant. The material was then cured at 75°±2° C. with 50±5% relative humidity for 21 days. The screen was then pulled from the surface in a 180° configuration using a Tinius Olson tensile machine at 2" rate per minute. The following pull measurements and percent cohesive failure were determined on 1" wide surfaces:

| Peel Adhesion Results | lbs./in. | % Cohesive Failure |
|---|---|---|
| Stainless Steel 304 | 32 | 65 |
| Anodized Aluminum | 44 | 95 |
| Plexiglass | 49 | 100 |
| Glass | 47 | 100 |
| Concrete | 50 | 100 |

This material was also found to show no visible sign of nodule formation after 4 years storage at room temperature (75° C.±2° C.).

EXAMPLE 4

Composition A—same as Example 3
Composition B—same as Example 3 except used titanium catalyst of Example 2
  Addition same as Example 3
  Physicals were

| Tensile Strength, psi | 210 | |
| Elongation, percent | 870 | |
| Shore A, hardness | 23 | |
| Tack Free Time, hrs. | 8.0 | |
| App. rate, grams/minute | 168 | |
| Flow rate, in. | 0.18 | |
| Specific gravity | 1.39 | |
| Peel Adhesion Results | lbs/in | % cohesive failure |
| Stainless steel | 53 | 100 |
| Anodized Aluminum | 48 | 100 |
| Plexiglass | 47 | 100 |
| Glass | 44 | 100 |
| Concrete | 44 | 100 |

This material was also found to show no visible sign of nodules after 4 years storage at room temperature.

EXAMPLE 5

Composition A—same as Example 3
Composition B—
There was prepared a Composition B as follows:
first to: 0.9 parts of 1,3-propane-dioxytitanium bis (ethyl acetoacetate) and 0.9 parts of 1,3-propane-dioxytitanium bis (acetyl acetonate) was added 1.5 parts methyltrimethoxysilane and 0.75 parts of 1,3,5-tris-trimethoxysilylpropylisocyanurate.

The addition was the same in Example 3
Physicals were:

| Tensile strength, psi | 240 | |
| Elongation, % | 800 | |
| Shore A, hardness | 25 | |
| Tack Free Time, hrs. | 7.5 hrs. | |
| App. Rate, grams/mins. | 190 g/min. | |
| Flow Rate, iveles | 0.10" | |
| Specific Gravity | 1.39 | |
| Peel Adhesion Results | lbs./in. | % cohesive failure |
| Stainless Steel | 38 | 75 |
| Anodized Aluminum | 51 | 100 |
| Plexiglass | 49 | 100 |
| Glass | 45 | 100 |
| Concrete | 47 | 100 |

This material also showed no visible sign of nodule formation after 4 years at room temperature.

We claim:

1. A titanium chelate catalyst for room temperature vulcanizable silicone rubber compositions which does not form nodules upon standing prior to cure comprising a first reaction product of a titanium compound of the formula, $$Ti(OR)_4$$

with a first ketone compound of the formula,

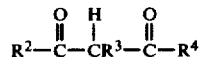

and with a second ketone compound of the formula

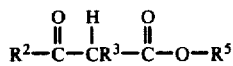

where R and $R^2$ are halogen substituted or unsubstituted monovalent hyudrocarbon radicals, $R^3$ is selected from the group consisting of hydrogen, hydrocarbyl, halohydrocarbyl, and acyl, all not having more than 8 carbon atoms and taken together with $R^2$ forms together with the carbon atoms to which they are attached a cyclohydrocarbon substituent of not more than about 12 carbon atoms and chloro, nitro, acyl, cyano and carboxy ester substituted cyclic hydrocarbon substituents, $R^4$ is a radical selected from the class consisting of radicals having not more than about eight carbon atoms selected from the group consisting of hydrocarbyl halohydrocarbyl, cyanoalkyl, and amino and $R^5$ is selected from the group consisting of monovalent hydrocarbon radicals, amino, ether and polyether moieties of the formula, $$-(C_qH_{2q}O)_rR^{30}$$

where q varies from 2 to 4 and v varies from 1 to 20 and $R^{30}$ is a monovalent hydrocarbon radical; said first reaction product then being reacted with a diol of the formula $$HO—R^6—OH$$

to produce the second and final catalyst reaction product where $R^6$ is a divalent hydrocarbon radical of 2 to 20 carbon atoms.

2. The titanium chelate catalyst of claim 1 wherein the final reaction product catalyst has the formula,

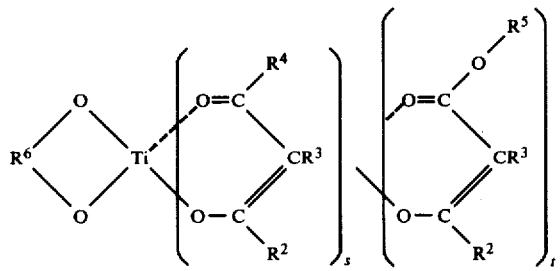

where s varies from 0.7 to 1.3 and t varies from 1.3 to 0.7.

3. The titanium chelate catalyst of claim 2 where s and t vary such that s varies from 0.8 to 1.2 and t varies from 1.2 to 0.8.

4. The titanium chelate catalyst of claim 3 wherein $R^6$ is propane.

5. The titanium chelate catalyst of claim 4 wherein the $R^3$ is hydrogen.

6. The titanium chelate catalyst of claim 4 where $R^2$ and $R^4$ are methyl.

7. The titanium chelate catalyst of claim 6 which has the formula,

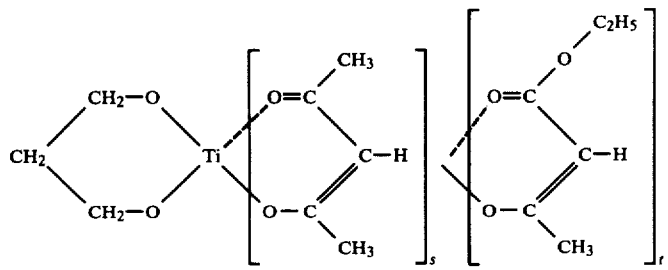

8. The titanium chelate catalyst of claim 7 wherein s is 1.0 and t is 1.0.

9. A method for forming a titanium chelate catalyst for room temperature vulcanizable silicone rubber compositions which does not form nodules upon prolonged storage comprising (1) reacting a titanium compound of the formula $$Ti(OR)_4$$

with a first ketone compound of the formula,

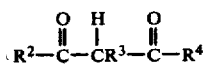

and with a second ketone compound of the formula, $$R^2—\overset{O}{\overset{\|}{C}}—CR^3—\overset{O}{\overset{\|}{C}}—O—R^5$$

where R and $R^2$ are halogen substituted or unsubstituted monovalent hydrocarbon radicals, $R^3$ is selected from the group consisting of hydrogen, hydrocarbyl, halohydrocarbyl and acyl, all having not more than 8 carbon atoms and taken together with $R^2$ form together with the carbon atoms to which they are attached a cyclic hydrocarbon substituent of not more than about 12 carbon atoms and chloro, nitro, acyl, cyano, and carboxy ester substituted cyclic hydrocarbon substituents, $R^4$ is a radical selected from the class consisting of radicals having not more than about eight carbon atoms selected from the group consisting of hydrocarbyl, halohydrocarbyl, cyanoalkyl, and amino and $R^5$ is selected from the group consisting of monovalent hydrocarbon radicals, amino, ether and polyether moieties of the formula, $$—(C_qH_{2q}O)_vR^{30}$$

where q varies from 2 to 4 and v varies from 1 to 20 and $R^{30}$ is a monovalent hydrocarbon radical and (2) reacting the first reaction product with a diol of the formula, $$HO—R^6—OH$$

to produce the second and final catalyst reaction product where $R^6$ is a divalent hydrocarbon radical of 2 to 20 carbon atoms.

10. The method of claim 9 wherein there is utilized a solvent in reaction (1).

11. The method of claim 10 wherein there is reacted 1 mole of the titanium compound with 1 mole of the first ketone compound and with 1 mole of the second ketone compound and wherein such first reaction product is reacted with one mole of the diol.

12. The method of claim 11 wherein the second reaction product has the formula,

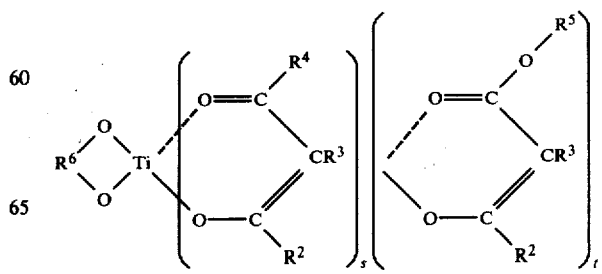

where s varies from 0.7 to 1.3 and t varies from 0.7 to 1.3.

13. The method of claim 12 wherein in the second reaction products formula, s varies from 0.8 to 1.2 and t varies from 1.2 to 0.8.

14. The method of claim 13 wherein in the formula of the titanium chelate reaction product $R^6$ is propane.

15. The method of claim 14 wherein the radical $R^3$ is hydrogen.

16. The method of claim 15 wherein $R^2$ and $R^4$ are methyl.

17. The method of claim 16 wherein the final reaction product titanium chelate catalyst has the formula,

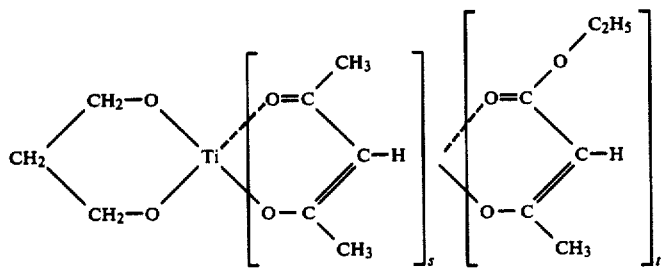

18. The method of claim 17 wherein s is 1.0 and t is 1.0.

19. A titanium chelate catalyst for room temperature vulcanizable silicone rubber compositions which does not form nodules upon prolonged storage comprising a physical blend of a first titanium catalyst of the formula,

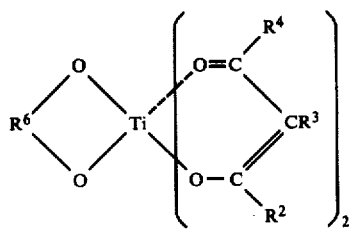

and a second titanium catalyst of the formula,

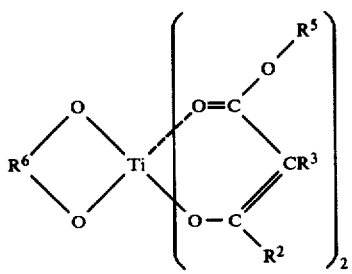

where $R^2$ is a halogen substituted or unsubstituted monovalent hydrocarbon radical, $R^3$ is selected from the group consisting of hydrogen, hydrocarbyl, halohydrocarbyl and acyl, none of which have more than about 8 carbon atoms and taken together with $R^2$ forms together with the carbon atoms to which they are attached a cyclohydrocarbon substituent of not more than about 12 carbon atoms and chloro, nitro, acyl, cyano and carboxy ester substituted cyclic hydrocarbon substituents, $R^4$ is a radical selected from the class consisting of radicals having not more than about eight carbon atoms selected from the group consisting of hydrocarbyl, halohydrocarbyl, cyanoalkyl, and amino and $R^5$ is selected from the group consisting of monovalent hydrocarbon radicals, amino, ether and polyether moieties of the formula

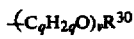

where q varies from 2 to 4 and v varies from 1 to 20 and $R^{30}$ is a monovalent hydrocarbon radical and $R^6$ is a divalent hydrocarbon radical of 2 to 20 carbon atoms, and wherein there is present 35 to 65 mole percent of the first catalyst and 65 to 35 mole percent of the second catalyst.

20. A process for forming a titanium chelate catalyst for room temperature vulcanizable silicone rubber compositions which does not form nodules upon standing prior to cure comprising mixing a first titanium chelate catalyst of the formula,

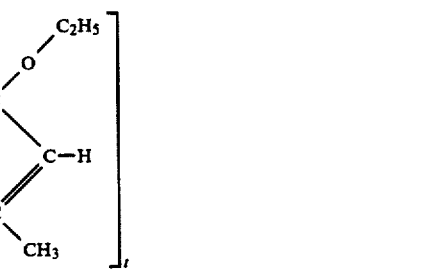

with a second titanium chelate catalyst of the formula,

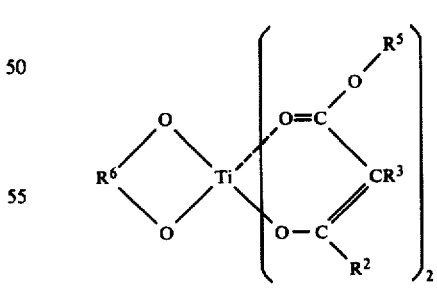

where $R^2$ is a halogen substituted or unsubstituted monovalent hydrocarbon radical, $R^3$ is selected from the group consisting of hydrogen, hydrocarbyl, halohydrocarbyl and acyl, none of which have more than about 8 carbon atoms and taken together with $R^2$ forms together with the carbon atoms to which they are attached a cyclohydrocarbon substituent of not more than about 12 carbon atoms and chloro, nitro, acyl, cyano and carboxy ester substituted cyclic hydrocarbon substituents, $R^4$ is a radical selected from the class consisting of radicals having not more than about 8 carbon atoms selected from the group consisting of hydrocarbyl, halohydrocarbyl, cyanoalkyl, and amino and $R^5$ is selected from the group consisting of monovalent hydrocarbon radicals, amino, ether and polyether moieties of the formula

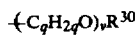

where q varies from 2 to 4 and v varies from 1 to 20 and $R^{30}$ is a monovalent hydrocarbon radical and $R^6$ is a divalent hydrocarbon radical of 2 to 20 carbon atoms, and wherein there is present from 35 to 65 mole percent of the first catalyst and 65 to 35 mole percent of the second catalyst.

21. The titanium chelate catalyst of claim 1 wherein the hydrocarbyl radicals are alkyl radicals and the halohydrocarbyl radicals are haloalkyl radicals.

22. The method of claim 9 wherein the hydrocarbyl radicals are alkyl radicals and the halohydrocarbyl radicals are haloalkyl radicals.

23. The titanium chelate catalyst of claim 19 wherein the hydrocarbyl radicals are alkyl radicals and the halohydrocarbyl radicals are haloalkyl radicals.

24. The process of claim 20 wherein the hydrocarbyl radicals are alkyl radicals and the halohydrocarbyl radicals are haloalkyl radicals.

25. The method of claim 10 wherein the solvent is toluene.

* * * * *